United States Patent [19]

Leisman et al.

[11] Patent Number: 4,686,983

[45] Date of Patent: Aug. 18, 1987

[54] APPARATUS AND METHOD FOR LIGATING A BODY VESSEL

[76] Inventors: Gerald Leisman, 130-12 - 229th St., Laurelton, N.Y. 11413; A. Zeev Hed, 12 Wagon Trail Dr., Nashua, N.H. 03062

[21] Appl. No.: 849,570

[22] Filed: Apr. 8, 1986

[51] Int. Cl.⁴ .................................. A61B 17/12
[52] U.S. Cl. ................................ 128/325; 128/321
[58] Field of Search ................ 128/325, 334 C, 321, 128/326, 346, 330, 322; 227/DIG. 1; 29/243.56; 72/410

[56] References Cited

U.S. PATENT DOCUMENTS

| | | | |
|---|---|---|---|
| 147,367 | 2/1874 | Burger | 128/330 X |
| 3,916,908 | 11/1975 | Leveen | 129/346 |
| 3,924,629 | 12/1975 | Akiyama | 128/325 |
| 4,506,670 | 3/1985 | Crossley | 128/334 C X |
| 4,570,633 | 2/1986 | Golden | 128/325 |

FOREIGN PATENT DOCUMENTS 2128478  5/1984  United Kingdom ............... 128/325

Primary Examiner—Michael H. Thaler
Attorney, Agent, or Firm—Eliot S. Gerber

[57] ABSTRACT

A ligating device for the ligation of blood vessels during surgery includes a clip assembly and an applicator. The clip assembly comprises two separate clip members which are interlocked on the vessel when the applicator is closed and which remains on the vessel when the applicator is reopened. The applicator includes opposite jaw portions, each of which retains a clip member in a deformable cavity, the jaw portions having flexible retaining legs, and the cavity being deformed to its open position when the jaws are closed.

32 Claims, 30 Drawing Figures

FIG. 8A  FIG. 8B  FIG. 8C
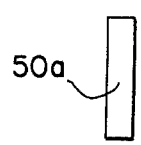
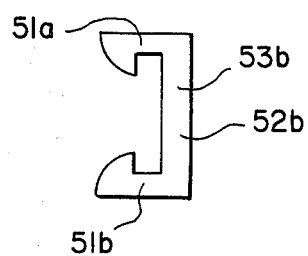
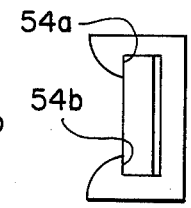
FIG. 9A  FIG. 9B
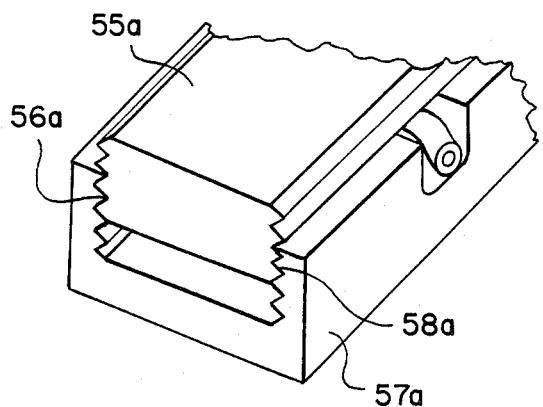
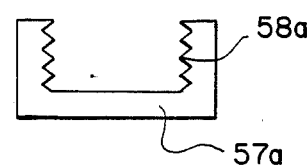

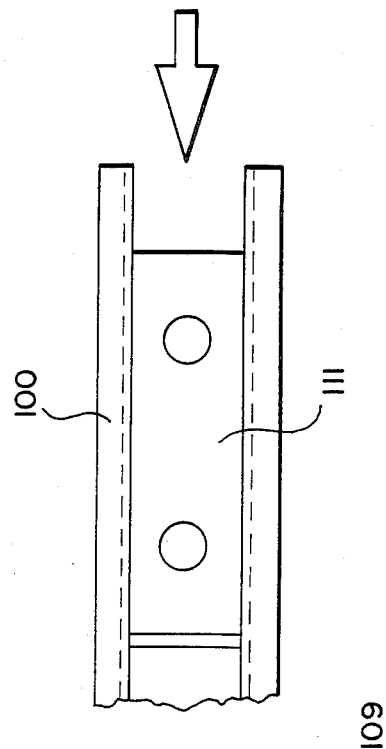
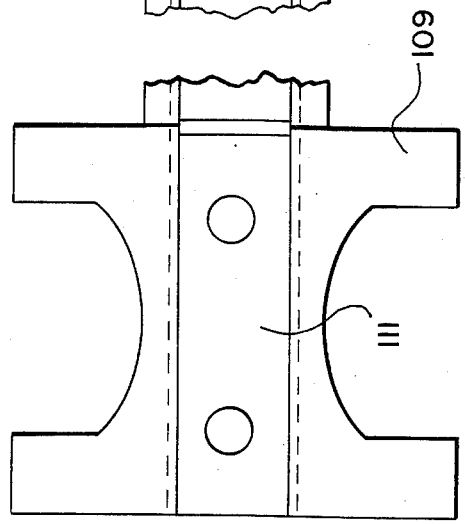

APPARATUS AND METHOD FOR LIGATING A BODY VESSEL

BACKGROUND OF THE INVENTION

1. Field of the Invention

This invention relates to an appartus and method for closing a severed body vessel such as a blood vessel, and more particularly to a method and apparatus for closing a body vessel using a pair of interfitting clip members.

2. Description of the Prior Art

The conventional method for ligating a blood vessel is that a cut end of the blood vessel is manually sutured, i.e., stitched using a thread-like material. In a surgical procedure, to avoid excessive bleeding, the cut ends of the blood vessels or tissue must be ligated quickly and certainly. If the surgeon is not skilled, the operating conditions are difficult or the vessel is not easily accessible, he may not be able to quickly and positively ligate the cut end of the blood vessel using suture material, i.e., tie a knot in the joined ends of the suture. In the conventional method, using suture, two operations are usually required, one to apply a hemostat to clamp the cut end of the vessel and the other to ligate the blood vessel to stop bleeding. For example, when the cut end of the blood vessel is beyond the reach of the surgeon's hand, it may be time-consuming, or even impossible, to suture the cut end of the blood vessel. Consequently, conventional suturing is very troublesome and difficult.

An alternative to ligation, using suture material, is to place a metal "U" shaped clip, sometimes called a "ligating clip", around the blood vessel and then to bring the arms of the clip together using an instrument having a closed action like a pair of pliers. The application of the clip to a blood vessel consits of deforming the "U" shaped clip by pressure around the vessel until the two arms of the clip are in close proximity and causes the complete closure of the blood vessel. In most cases the clips are made of deformable and biocompatible metals such as stainless steel, tantalum and titanium. One such method is shown in U.S. Pat. No. 2,301,622 entitled "Hemostat" and another is shown in U.S. Pat. No. 3,270,745 entitled "Hemostatic Clip Constructions". Many surgeons, however, are still avoiding the use of metal mechanical clip ligating devices, as they present a number of important shortcomings. Such clips generally lack an absolutely secure attachment of the ligating clip to the applicator prior to ligation, for example, when being tranferred between assisting personnel and the surgeon. They may fall off before being used, or may even fall into the patient's body cavity, i.e., into the surgical opening, since the clips are held in the applying instrument by pressure from the jaws, which may be easily disrupted. Applying the clip to the body vessel is difficult because of the fixed and usually small aperture of the applicator. In addition, the applicator is generally a cumbersome device which may be difficult to master.

The use of two-piece plastic clamps or clips of various constuction has been suggested by the patent literature for use in surgery.

In U.S. Pat. No. 3,924,629 entitled "Method For Closing A Cut End Of A Blood Vessel", a two-piece plastic clamp is closed by end flaps which are pushed over the ends of a mating clamp plate. The clamp plates are held in strips in a tool.

A two-piece clamp is shown in U.S. Pat. No. 3,744,495 entitled "Method of Securing Prolapsed Vagina in Cattle". The legs of the clamp members are held in slots in each half of the tool case. The clamp is removed from the tool, after closure, by sliding it out from the slot.

In British Pat. No. 972,371, at FIGS. 1 and 2, a two-piece clamp is used as an artery clamp. The clamp is made of protein-base plastic material absorbable by the living tissue. The two clamp members are locked by deformable arrow-shaped heads and cooperating apertures.

In U.S. Pat. No. 3,916,908 entitled "Disposable Bowel Clamp and Detachable Applicator", a plastic two-piece clamp has two rod members each having a male and female hooking means at their ends. The rod members are frictionally held in their respective jaws until they are clamped together.

SUMMARY OF THE INVENTION

In practicing the present invention, a cut end of a blood vessel is closed by applying a hemostat to the cut end of the blood vessel between a pair of plastic clip members and fastening the pair of clip members to each other.

An apparatus for carrying out the above method comprises a pair of actuating members adapted to engage the pair of clip members, press the pair of clip members against one another with the cut end of the blood vessel between them and concurrently to fasten the two members of the pair together, and then release the actuating members from the clip members.

OBJECTIVES AND FEATURES OF THE INVENTION

It is an objective of the present invention to provide a novel method for closing a cut end of a body tissue, such as a blood vessel, using a pair of clip members which are fatened together and released from their applicator.

A still further objective of one embodiment of the present invention is to provide an apparatus which will carry a series of the clip members which are intermittently advanced, one after the other, to the applying end of the applicator.

A still further objective of the present invention is to provide an apparatus for closing the cut end of the body vessel which can be operated reliably, simply and rapidly.

A still further objective of the present invention is to provide an apparatus for closing the cut end of the body vessel which is simple in construction, so that it may be relatively low in cost and relatively less proned to mechanical failure.

It is a feature of the present invention to provide a ligating apparatus and method to ligate a body vessel. The apparatus and method utilizes, in some of its embodiments, a hemostat-like (plier-like) applicator having, as portions thereof, first and second elongated members. Each of the elongated members has a handle portion and a jaw portion. The applicator further includes means to move the first and second elongated members so that the jaws may be closed together and then opened.

A ligating clip assembly comprises, as separate members, a first and second clip member, both preferably of plastic. Each clip member has a rod body portion and means on opposite ends of each body portion to interlock said clip member with the other clip member upon clamping the clip members together, such as a boss on one end and a hole on the opposite end of the body portion.

Retaining means on each jaw portion retains one of said clip members in one of said jaw portions prior to closing the jaws and expels it from the jaw portion upon closing said jaw portions. The retaining means includes flexible retaining legs on opposite sides of each of clip members. The legs are positioned opposite corresponding legs on the other jaw portion. The legs, upon closing of the jaws, are spread apart and release the clip members from the jaw portions. The jaw portions are then opened and leave the clip members closed and clamped on said vessel.

It is a further feature of the present invention that each jaw portion has a cavity to retain a clip member, with the legs on opposite sides of the cavity and the cavity is a curved sector in original shape and is flattened out upon closure of the jaws to expel the clip members.

In one embodiment the jaw portion is formed as an integral portion of the applicator. In another embodiment the jaw portions are formed as separate heads which fit over the distal ends of hemostats or similar hinged instruments.

The clip members may be retained in the retaining means either by friction of by a flange (rail) and groove system.

BRIEF DESCRIPTION OF THE DRAWINGS

Other objectives and features of the present invention will be apparent from the following detailed description of the invention taken in conjunction with the accompanying drawings.

In the drawings:

FIG. 6 is a drawing of the first embodiment of the clip assembly, in which

FIGS. 8 is a still further alternative embodiment of a clip assembly, in which FIG. 8A is a side plan view of the left-hand clip member, FIG. 8B is side plan view of the right-hand clip member, and FIG. 8C is an assembly view in which the left-hand clip member has been captured and clamped within the right-hand clip member; FIG. 8D is an alternative embodiment in which the left-hand clip member is captured and clamped on its long sides by the right-handed clip member;

FIG. 9 is a still further embodiment of an alternative clip structure, in which FIG. 9A is a perspective enlarged partial view of the left-hand and right-hand clip members assembled, and FIG. 9B is a front plan view of the right-hand clip member;

FIG. 10C is an alterative enlarged side front view of a jaw portion, in which

FIGS. 13 and 14 are enlarged front plan views of alternative head portions, in which FIG. 13 is prior to closure and FIG. 14 is during closure.

FIG. 17 is an enlarged plan view of a series of clips in the feeding mechanism of the embodiment of FIG. 16.

DETAILED DESCRIPTION OF THE INVENTION

Figure 1:
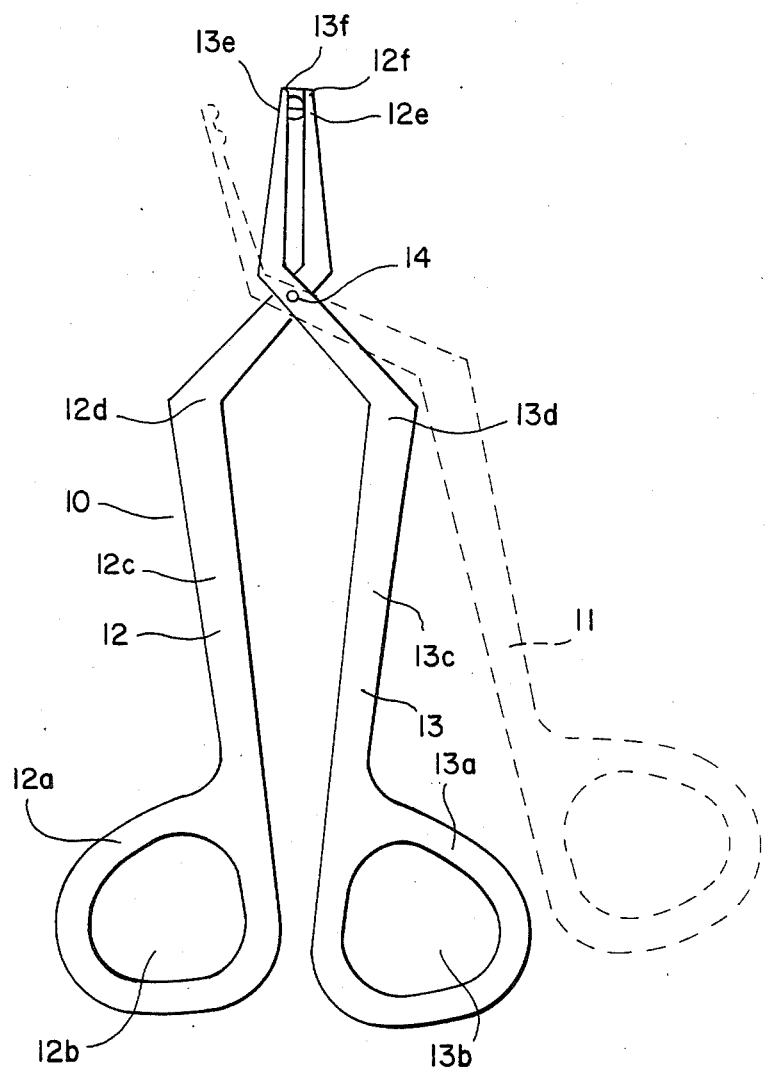
FIG. 1 is a top plan view of the applicator of the first embodiment of the invention.

The first embodiment of the present invention is a disposable applicator and is illustrated in FIGS. 1 through 4. As shown in FIG. 1, the applicator 10 and the clip members 32,33 are manufactured and sold as a complete unit. For example, each applicator with its attached clip members may be enclosed in a sterile container, for example, paper or plastic container.

In FIG. 1 the applicator is shown in its open position in dotted lines and in its closed position in full lines. The applicator 10 in some respects resembles a conventional hemostat. When the surgeon's assistant opens the package, it will contain the applicator 10 in its open position, shown in the dotted lines 11.

In the embodiments, as illustrated, the applicator is shown as having a plier-like (scissor-like) action, i.e., a pivot. However, the applictor may have other forms, such as a spring-action tweezer, in which the jaws may be manually closed then opened.

In the embodiment of FIG. 1, the applicator 10 consists of an elongated left handle member 12 and an elongated right handle member 13. The left handle member has, as integral portions thereof, a finger loop portion 12a having a hole 12b therethrough to fit a finger, and a shaft portion 12c. The shaft portion 12c is bent at turn portion 12d and is hinged to the right applicator handle 13 by hinge pin 14 to provide a plier-like action. A jaw portion 12e is integral with the shaft portion 12c and extends to the distal end 12f. Similarly, the right handle member has finger loop portion 13a having hole 13b, a shaft portion 13c, a turn portion 13d, a jaw portion 13e and a distal end 13f.

A number of alternative clip members, having different configurations and different sizes, may be used in the cavities of the jaw portions 12e-13e, depending on the size and shape of the jaw portions.

In general, in the below-described embodiments the clip members are held within the cavities of the jaw portions either by pressure fitting or by a rail system. In operation, the jaw members are closed, which interlocks the clip members, and then the jaw members are spread open, which frees the clip members. The clip members are clamped together and interlock, for example, by male and female protrusions and recesses, rspectively, on the two clip members.

Figure 2:
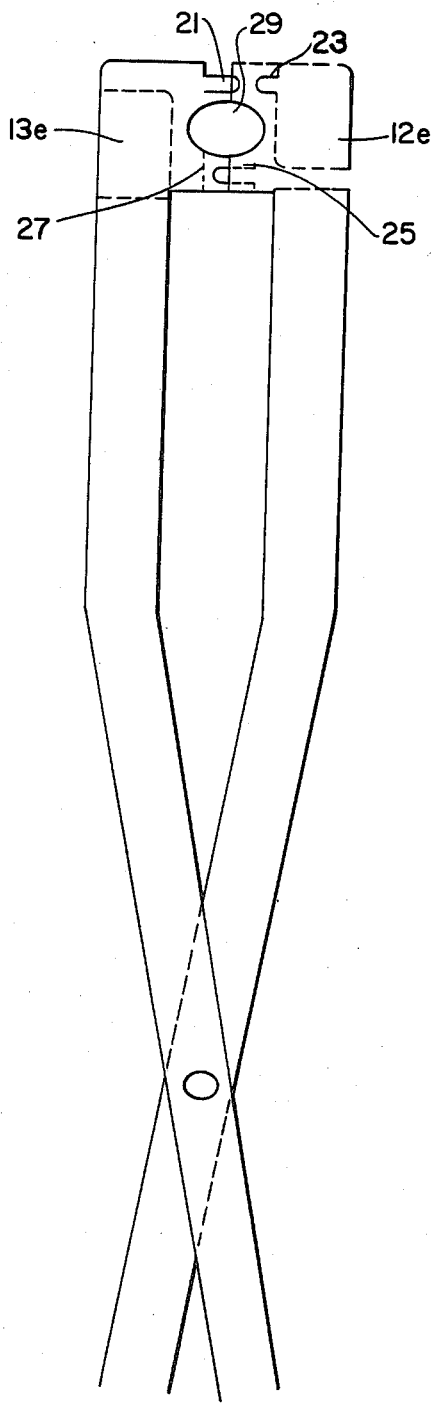
FIG. 2 is a top plan view, enlarged, of the jaw portion of the applicator of FIG. 1.
Figure 3:
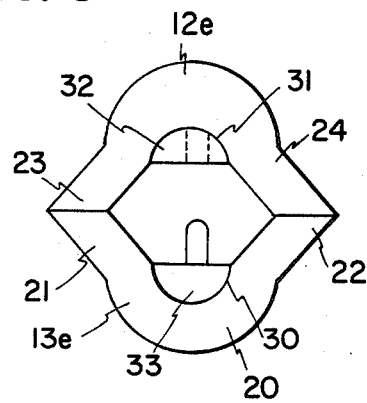
FIG. 3 is a front plan view, enlarged, of the jaw portion of the applicator of FIG. 1 prior to closure.

In the embodiment of FIG. 2, the distal ends of the jaw portions are shown enlarged. As illustrated in FIG. 3, the jaw portion 13e has a body portion 20 with opposite flexible front legs 23 and 24. Each of the frontal legs 21-24 are at the distal end of the applicator. A similar set of rear legs 25 are separated from the legs 20-24 by the open gap 29.

The legs 21-24 and 25 are arranged so that when the applicator is started to be closed, shown in FIG. 3, each leg will touch its opposite leg, for example, the free end of leg 21 touches the free end of leg 23 and the free end of legs 23 touches the free end of leg 24.

The jaw portions 13e' and 12e' have nesting cavities, respectively, 30,31, in which are fit and nested the respective clip members 32,33. The details of construction of alternative embodiments of the clip members will be explained in connection with later figures.

Figure 4:
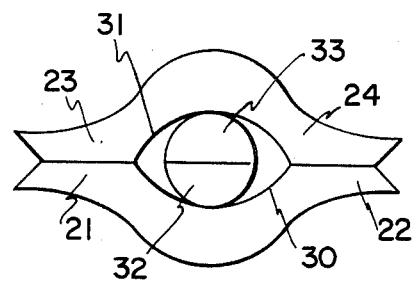
FIG. 4 is a front plan view, enlarged, of the jaw portion of the applicator of FIG. 1 during application.

As illustrated in FIG. 4, the clips 32, 33 are pressure-fit held in cavities 30,31. When the applicator 10 is in its fully closed position, the respective legs 21-24 and 25 are spread outwardly. This causes the cavities 30,31 to open up, i.e., to be deformed, for example, from a semicircular shape to an ellipsoidal sector shape, which deformation frees and releases the clip members 32,33. When the jaws of the applicator are opened, after the clip members have been clamped together, the cavity walls will act to push the clip members from their nesting positions, that is, the cavity walls will force the clip members away from the jaw portions of the applicator. The clip members will be clamped and remain on the blood vessel. The clip members will be freed of the applicator and the applicator will then be removed from the surgical field.

In this embodiment of the invention, the jaws of the applicator are the jaws of a hemostat-like applicator. A hemostat-like structure is preferred as the applicator because is it used by surgeons. There is no need for re-education of the surgeons in the application of the clip since its application mimics the hemostat action. The disposable applicator removes a potential encrumbrance from the operating room, namely, loading the clips on the applicator.

The form of the disposable applicator can be any of the variety of hemostats, clamps, forceps and pliers that are currently used. The disposable applicator only requires two arms that can easily be brought together and used to apply the necessary pressure on the jaws to deform the legs and cause the two clip members to be clamped together.

Figure 5A:
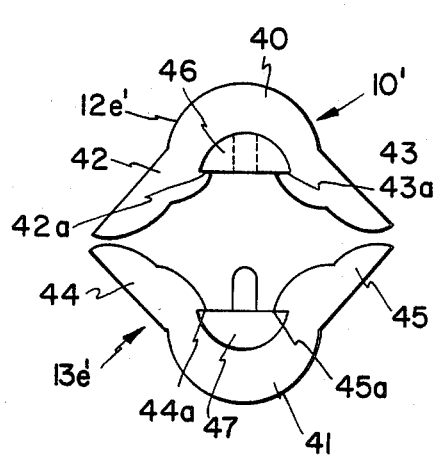
FIG. 5A is a front plan view, enlarged, of the jaw portion of an alternative embodiment of the present invention prior to closure.
Figure 5B:
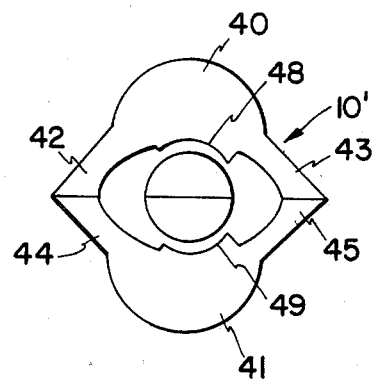
FIG. 5B is a front plan view, enlarged, of the jaw portion of FIG. 5 during closure.
Figure 6A:
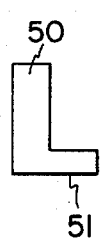
FIG. 6A is a side plan view of the left-hand member.
Figure 6B:
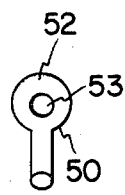
FIG. 6B is a top plan view of the left-hand member.
Figure 6C:
FIG. 6C is a top plan view of the right-hand member.
Figure 6D:
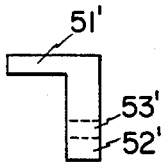
FIG. 6D is a side plan view of the right-hand member.

An alternative embodiment of an applicator to hold the clip members in positions within the applicator and to prevent their accidental removal from the applicator until the applicator jaw is deliberately closed by the user, is illustrated in connection with FIGS. 5, 6 and 7. As illustrated in FIG. 5, in the applicator 10' the jaw portions 12e" and 13e" have an exterior dome shape 40-41. In this embodiment, the forward legs 42 and 43 of the jaw portion 12e' and the forward legs 44 and 45 of the jaw portion 13e each have undercut ledges 42a-45a. These ledges form rails and act to positively support the respective clip members 46 and 47 in their cavities. As illustrated in FIG. 6, when the applicator 10' is fully closed, the nesting cavities 48 and 49 will open up, that is, in cross-section their curve is flattened. When the applicator jaws are closed, leg 42 pushes against the leg 44 and simultaneously leg 43 pushes against leg 45. As in the prior embodiment, the clip members 46 and 47 are firmly clamped together when the applicator is closed. The opening of the legs, which are flexible members, by being cammed by the opposite leg, frees the clip members from the grip of the rails formed by the legs 42a-45a. It will be understood, although not illustrated in FIGS. 5A and 5B, that the forward legs 42-45 are in front of two similar pairs of rearward legs having the same structure and function as the legs 42-45. The forward and rearward position of these four pairs of legs is similar to that shown in FIG. 2. Two of the legs provide the opening for the healthy body vessel. Consequently, the opposite two legs may be joined to form a wall, i.e., front legs 42 and rear leg 44 are separate; but front leg 43 and rear leg 45 may be joined.

The above-described tongue-rail system for holding and releasing the clip members in and from the jaw, prior to and during the applicatin of the clip, differs in one respect from the pressure-fit embodiments described above. In the rail systems the securing of clip members does not depend solely on the pressure applied to the member by the cavity wall. In one rail clip holding embodiment, the four legs have longitudinal ledges (protrusions) extending slightly into the plane of contact (about 5% to 10% fo the plane of contact's width), creating two segmented railings, thus providing a more positive holding of the clip member. The cavity cross-section can now be exactly as the clip member cross-section or even a little larger (but not so large that the clip member can be free to rock inside the cavity). To prevent the loss of the number by sliding either forward or backward in the cavity, a partial closue of the front and back is provided. In the front this closure is a simple rim around part or all of the circumference of the cavity but excluding the line formed by the plane of contact. In the back a dynamic closure of a rim as in the front may be used. The loading of the members in the head, performed usually at the factory, is either by sliding or pressing in. In use, by pressing the two jaw portions together, the legs, to which the ledges (longitudinal protrusions) are attached, are forced to part, and the railings are forced to part as well, releasing the clip members to clamp onto each other. When the pressure on the forcing top is released, the legs spring back onto the partially released clip, forcing the clamped clip completely out of the jaws. A preferred choice of clips for the ledge-rail embodiments will have clips whose plane of contact is larger than any other plane parallel to itself within the clip. This facilities the spring-back action and completes the forcing down of the clip members out of their cavities.

In the embodiments so far described, the clip members have been shown as each having a rear semi-cylindrical shape so as to fit an originally semi-cylindrical shaped nesting cavity. It will be understood, however, that alternative types of two-piece clips may be used. Certain alternative embodiments of the two-piece clips are shown in FIGS. 6-10.

In the clip assembly of FIG. 6, a rod body portion 50 on the left clip has an L-shaped male boss portion 51 at one of its ends and a ring-like portion 52 having a hole therethrough 53 at its other end. Similarly, the right clip member 50' has a boss portion 51' and the ring-like portion 52'. The boss portions 51, 51' may have enlarged end heads (not shown). When the clip members are clamped closed, the boss portion 51' fits within the hole 53'. The clip members are held together by friction and/or the enlarged end heads of the boss portions 51,51'.

The clip assembly of FIG. 7 is similar in some respects to the clip assembly of FIG. 6, except only the left clip member is shown. It will be understood, however, that the right clip member is a mirror image of the left clip member. The left clip member 55 has a protruding boss 56 which is round in cross-section. The rod-like body portion 58, at its opposite end, has a hole therethough 59 which is adapted to receive the boss of the right clip member. The rod body portions of the left and right clips, as seen in cross-section, may be of various shapes. In the embodiment of FIGS. 3 and 4 they are semi-circular in cross-section; in the embodiment of FIGS. 6 and 7 they are rectangular in cross-section; and in the embodiment of FIGS. 11-14 they are trapezoidal in cross-section.

Figure 7A:
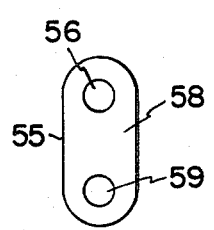
FIG. 7A is a top plan view of an alternative clip member, the left-hand member being shown and the right-hand member being a mirror image.
Figure 7B:
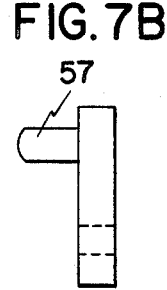
FIG. 7B is a side plan view of the clip member of FIG. 7A.
Figure 7C:
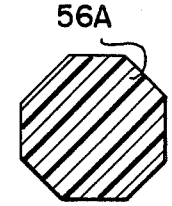
FIGS. 7C and 7D are enlarged cross-sectional views of alternative boss portions.

An alternative boss construction is shown in FIGS. 7C in an enlarged cross-sectional view of the boss. The boss 56a is octangonal in shape and fits into an octagon-shaped hole.

Figure 7D:
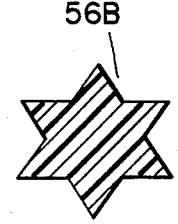

A still further embodiment of a boss is shown in FIG. 7D, in which the boss 56D is shown as a six-pointed star. The six-pointed star boss would fit into a corresponding six-pointed hole. Alternatively, the boss may have other polygonal or curved cross-sectional shapes.

The clip members shown in FIG. 8 consist of a right handed clip member 50a, which is a rectangular block, and left-handed clip member 52b. The clip member 52b has a body portion 53b which terminates in two opposite upstanding end arms 51a and 51b. Each of the arms 51a,51b has an enlarged knob portion forming an undercut ledge, 54a and 54b respectively. The arm portions 51a and 51b are pushed outwardly by the insertion of left clip member 50a and ledges 54a and 54b trap and retain the left clip member within the right clip member when the two clip members are clamped together. In the illustrated embodiments, the plane of contact (contact surface) of the clip members with the body vessel is smooth; alternatively, and not shown, the contact surface may have bumps, like a bed of nails, or flexible bumps, which contact and hold the body vessel.

In the embodiment of the alternative construction of the clip member shown in FIG. 9, the left clip member 55a is a rectangular member having serrated opposite side edges 56a. The right clip member 57a has internal channel having internal opposite walls having serrated edges 58a. The serrated edges 58a of the channel interlock with the serrated sidewalls 56a of the left clip member 55a to retain the left clip member within the cavity of the right clip member.

In the following embodiments the clip members are removably retained in the jaw portions by friction, and not by a ledge-rail system. When the legs of the opposite jaw portions are brought together, on closure of the apparatus, the legs are spread outward and release the clip members from the jaw portions.

Figure 10A:
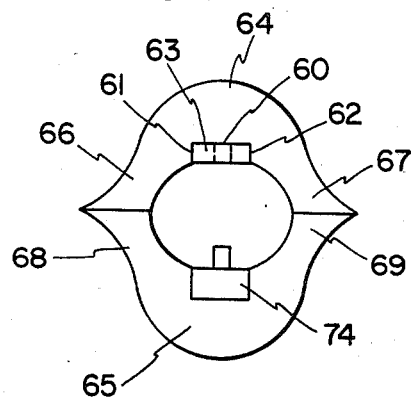
FIG. 10A illustrates the jaw portion prior to closure and FIG. 10B illustrates the jaw portion during closure.
Figure 10B:
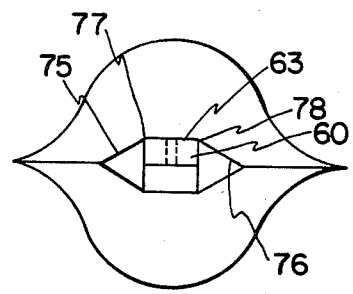
Figure 10C:
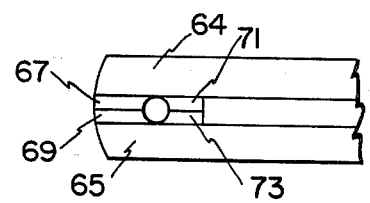

As shown in FIG. 10, the upper clip member 60 has opposite side walls 61,62 which are frictionally gripped by the internal side walls of the cavity 63 of the jaw portion 64. The opposite clip member 74 and opposite jaw portion 65 have the same construction, size and parts as the clip member 60 and jaw portion 64, respectively, jaw portions 64, 65 being shown in side view in FIG. 10C. The jaw portion 64 has forward flexible legs 66,67 which, upon closure, contact the opposite flexible forward legs 68,69 of jaw portion 65. Similarly, the flexible rear legs 70,71 of jaw portion 64 contact and spread the flexible rear legs 72,73 of jaw portion 65. When the jaws are completely closed, as shown in FIG. 10B, the inner side walls of the cavity 63 are opened and release the clip member 60. When the jaws are re-opened, after closure, the slanted side walls 75,76 cam against the corners 77,78 of the clip member 60 and expel it from the jaw member. As in the prior embodiments, the clamped and interlocked clip members 60,74 remain clamped on the body vessel and the plier-like apparatus is removed from the surgical field.

In the following embodiments, the jaw portion is formed as separate plastic holding members which are adapted to be inserted on the ends of standard metal surgical hemostats. In these embodiments, the jaw members are disposable, i.e., the head is disposable. Each of the jaw member heads removably retains a clip member. The surgeon's assistant inserts the prongs of the distal end of the hemostat into corresponding recesses in the plastic heads, with the jaws of the hemostat opened. The surgeon, as in the prior embodiments, will close the jaws in order to bring the two clip members together and interlock the clip members with the body vessel clamped between the two clip members. The surgeon will then open the jaws, which causes the clip members to be ejected from their seating cavities in their respective jaw members.

Figure 11:
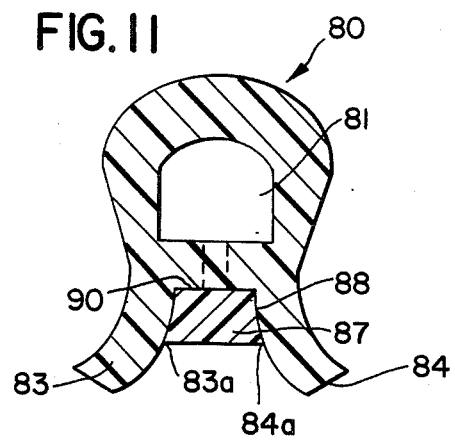
FIG. 11 is a head portion which is an enlarged cross-sectional view of a still further embodiment of the invention taken along line A—A of FIG. 12.
Figure 12:
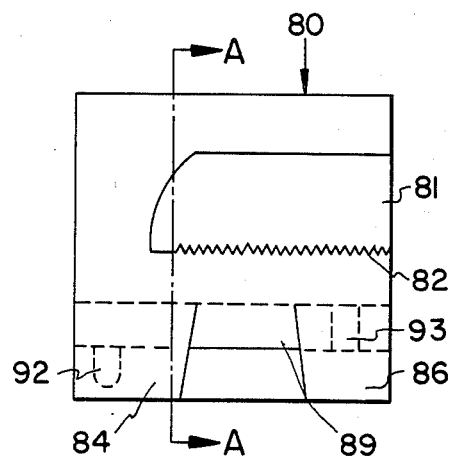
FIG. 12 is a side cross-sectional view of a head portion.

FIGS. 11 and 12 illustrate one embodiment of a plastic jaw member. It will be understood, however, that the complete system includes two such jaw members, with one jaw member fitting on each prong end of a standard metal hemostat. The plastic jaw member 80 includes an internal first cavity 81 having a serrated bottom wall 82. The cavity 81 firmly retains the prong end of a hemostat. The jaw member 80 has a pair of flexible forward feet 83,84 and a pair of rearward flexible feet 85,86. A first clip member 87 is removably retained in the second cavity 88 and is held in the cavity 88 by ledges 83a,84a of the legs 83-86. For example, the clip member may be any of the types of clip described above. As shown in FIGS. 11 and 12, the clip member 87 has a rod portion 89 having a flat top portion 90, a flat bottom portion 91, a boss portion 92 near one end of the rod portion 89, and a hole 93 near the opposite end of the rod portion.

Figure 13:
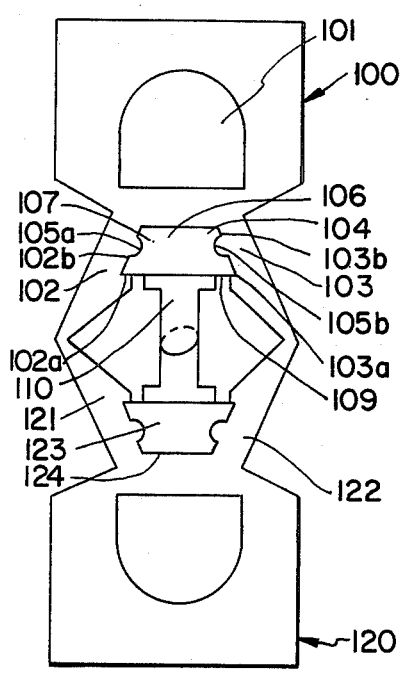
Figure 14:
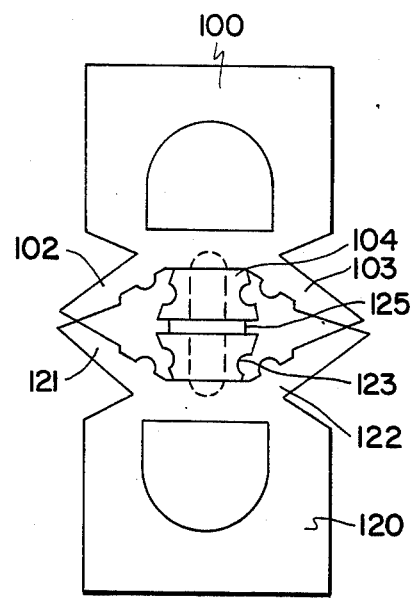

The embodiment illustrated in FIGS. 13 and 14 is also adapted to be inserted on the prong end of a hemostat. In this embodiment, however, the leg portions retain the clip member with two ledges (rails), one above the other.

As in the prior embodiment, the complete system includes two such jaw members 100 and 120, one on each prong end of a standard hemostat. The first plastic jaw member 100 includes an internal first cavity 101 having a serrated bottom wall which firmly retains the prong end of a hemostat. The jaw member 101 has a pair of flexible forward legs 102,203 and a pair of rearward flexible legs (not shown). A first clip member 104 is removably retained in the second cavity 105 and is held in the cavity 105 by the ledges 102a-103a. In addition, a protrusion 102b-103b fits within indentations 105a-105b of the clip member 106, to form a second rail retaining system. For example, the clip member 106 may be any of the types of clip members described above. As shown in FIGS. 13 and 14, the clip member 106 has a rod portion having flat top portion 108, a flat bottom portion 109, a boss portion 110 near one end, the rod portion 107 and a hole (not shown) near the opposite end of the rod portion.

As shown in FIG. 13, the legs 102, 103 are just starting to touch the legs 121, 122 of the second (bottom) clip member 120. The clip member 123 is removably retained in the second cavity 124 of the jaw member 120. When the jaw members 100, 120 are fully closed, as shown in FIG. 14, because the hemostat is clamped fully shut, the legs 102, 103 and 121, 122 are spread outwardly, which releases their respective clip members 104, 123. The ledges are released. The clip members 104, 123 are fully clamped together and interlocked, leaving a gap 125 due to the step construction of the clip members.

In the above-described disposable head method, the heads each have a depression (recess) in which the tip of a hemostat can be inserted. This recess should extend to about 80% of the length of the head or may create a fully open tunnel going through the head's full length. The cross-section of this recess will be identical to that of the tip of the applying hemostat.

In one embodiment the length of the head is the same as the length of the clip (between 3 and 12 mm). In another embodiment the recess part of the head can extend further back to create a sleeve around the arm of the applying instrument. The length of such a sleeve should be such that when loading the two heads on the applying instrument no error may occur in the final positioning of the two heads relative to each other. A special loading device to achieve this requirement is described below.

Preferably the clip members are loaded into the heads at the factory. Generally, for those hemostats having mirror image jaws, the heads are loaded on a base in two rows, one row of right heads and the other of left heads. The heads are aligned with their recesses pointing up. The head front part is fully supported by the base and the heads may be mounted in the base by a thin, easily deformable railing around the heads' legs. The heads are mounted at an appropriate spacing and angle to the vertical so that the hemostat's jaws (tips) can be simultaneously inserted into the two recesses. The loading action consists of inserting the hemostat tips firmly into the recesses until the resistance of the base is felt and then opening the instrument's jaws so as to release the head's lips from the deformable railings and thus from the base. The hemostat is now loaded, a small closure of the instrument will show to the applier some minimal and flexible resistance, a stronger closure will cause the simultaneous clamping of the two clip members and their release from their respective heads. Once the clips have been clamped, the two heads are discarded by pulling them off the tips of the hemostat.

The purpose of the multiple clip applicator is to feed, in sequence, an interrupted sequence of clip assemblies, prior to their being clamped together. The applicator is similar in some respects to a hemostat. The first clip assembly is clamped and then the surgeon reopens the jaws of the applicator. The opening of the jaws causes the next clip members to be pushed into respective cavities in the applicator's head.

Figure 16:
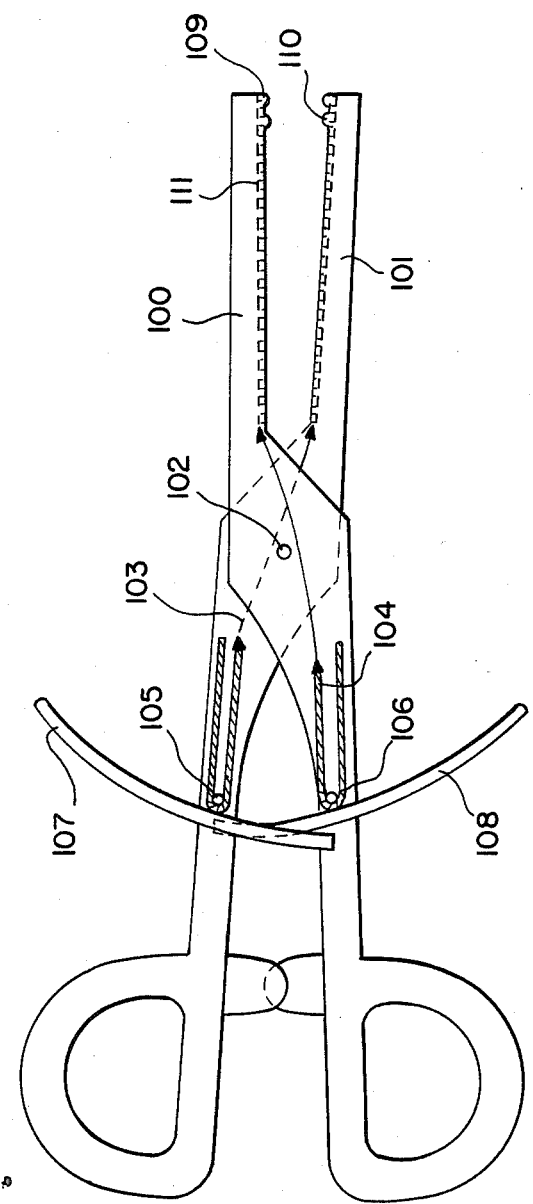
FIG. 16 is a top plan view of an applicator with an automatic feeding mechanism, partially in cross-section.
Figure 18:
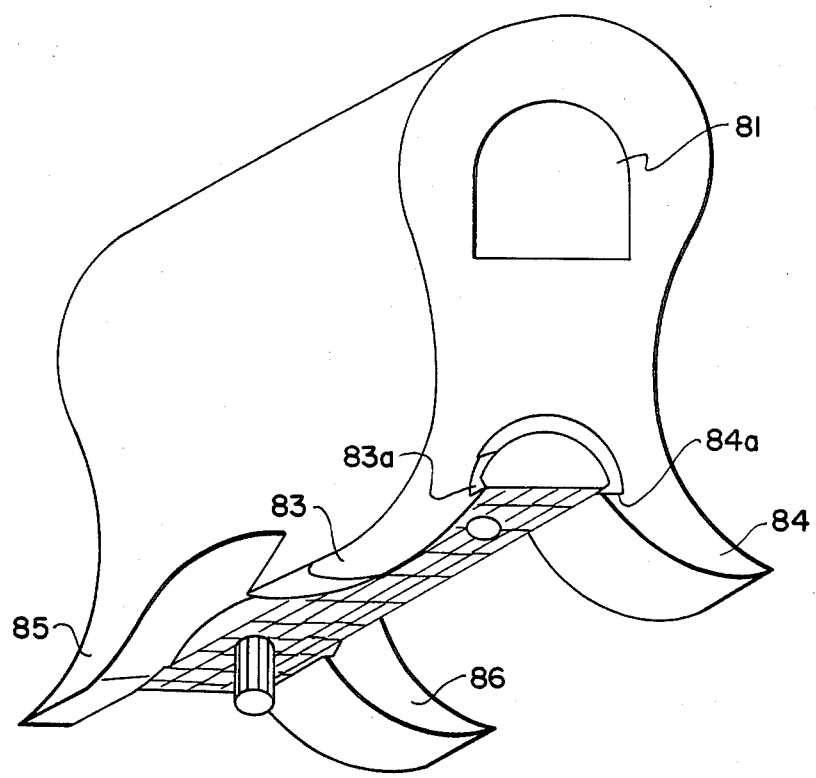
FIG. 18 is a perspective view of the head portion of the type shown in FIGS. 11 and 12 but with clips having curved top walls.

The structure of the applicator is based on the disposable applicator described above, which operates with two clip members and the ledge-rail type head. The arms of the applicator have an internal cross-section equal in geometry and slightly larger in dimensionl than the cross-section of the clip member 111, with the exception that the protrusion in the plane of contact extend toward each other, leaving an open space slightly larger than the clip member's boss. These structures, open toward the side opposing the second arm of the applicator, serve as a storage for the clip members. This storage area is terminated near the junction of the two applicator arms by a conduit that is fully enclosed. As shown in FIG. 16 the applicator arms 100, 101 are hollow from the conduit through the junction area and beyond. The cross-section of this conduit can be either rectangular or circular, depending on the pushing strip chosen to force the movement of the clip members to the applicator head. The conduits bypass the pivot (hub) 102 on which the two opposing members of the applicator pivot to provide the opening and closing action of the applicator's jaws. Inside the conduit two stiff but flexible strips 103, 104 push the clip members. This push strip is terminated on the head side of the clip members. On the handle side of the applicator this strip rolls against shafts 105, 106 or a semicircular structure, at the termination of the conduit. The rolling direction is from the inside of the applicator to the outside (inside being the space between the two arms and outside the space outside the two arms).

The handles of the applicator are equipped with arched members 107, 108. When the applicator is opened (in excess of a predetermined angle) the arched member 107, 108 presses the push strip 103, 104 to the semicircular structure terminating the conduit. When the applicator arms are opened (in an angle larger than the predetermined aperture) the arched member moves the strip by the friction between the arched member and the strip. The strip moves toward the head of the applicator and pushes the clip member to lodge itself in the bay. The yet unused part of the push strip is stored in a conduit, parallel to the first conduit, on the outer part of the handle.

The head 109, 110 has a cavity slightly larger than the clip member, and the cavity is terminated with a circumferential lip (described earlier) to avoid pushing the clip members out of the cavity. The arrest at the end of the bay provides for automatic positioning of the clip member. If the applicator arms are opened too far, or twice, it will have no effect on the strip and the clip member, because the arched member will slide over the strip. The structure and push strip described for one side of the applicator are utilized in a mirror manner on the other side.

Additional variations of the push mechanisms include a serrated strip and/or serrated arched member for better friction during the opening of the applicator or a unidirectional toothed wheel and toothed strip.

Since there is a one-to-one relationship between the length of the strip pushed up the conduit toward the applicator head and the number of clips already used, the strip can be premarked with either ascending or descending numbers indicating the number of clip members used or, alternatively, the number of clip members left in the applicator. A small window in the arms of the applicator can be provided to view such numbers.

What is claimed is:

1. A disposable ligating apparatus to ligate a body vessel comprising:
   an applicator having as portions thereof first and second elongated members each having a handle portion, a jaw portion, means to connect the portions of said first and second elongated members so that the jaw portions may be closed together and then spread;

a ligating clip assembly comprising as separate members a first and second clip member, each clip member having a body portion and means on each body portion to interlock said clip member with the other clip member upon clamping the clip members together;

retaining cavity means integral with each jaw portion to retain one of said clip members in said jaw portion prior to closing said jaw portion, which retaining cavity means is opened releasing the clip member upon closing said jaw portions;

flexible retaining legs on opposite sides of each of said cavity means, said legs being positioned opposite corresponding legs on the other jaw portion, the said legs upon closing of the jaw portions being spread apart releasing said clip members from said jaw portions by deformational opening of said retaining cavity means, said jaw portions on closure interlocking together said clip members, said jaw portions then being opened leaving said clip members closed and clamped on said vessel.

2. A ligating apparatus as in claim 1 wherein each of said jaw portions has a cavity portion to retain one of said clip members by frictional fit, said legs being on opposite sides of said cavity.

3. A ligating apparatus as in claim 2 wherein said cavity is a curved sector in original shape and is flattened out upon closure of said jaws to expel said clip member.

4. A ligating apparatus as in claim 3 wherein said cavity is originally a cylindrical sector and is flattened out to an elliptical sector.

5. A ligating apparatus as in claim 1 wherein each of said jaw portions has a cavity portion with a flange, each of said clip members has a channel which fits said flange to removably retain said clip member in said cavity, said legs being on opposite sides of said cavity.

6. A ligating apparatus as in claim 1 wherein each of said jaw portions has at least three legs, with two legs arranged on one side of the cavity.

7. A ligating apparatus as in claim 1 wherein said clip assembly is of a body-compatible plastic material which is absorbable in the body.

8. A ligating apparatus as in claim 1 wherein each of said clip members has a body portion and near one end thereof a male boss member and near the opposite end thereof a female indentation to interlock with the corresponding boss on the opposite clip member.

9. A ligating apparatus as in claim 1 wherein said applicator is of plastic.

10. A ligating apparatus as in claim 9 wherein each of said cavity portions has a flange, each of said clip members has a channel which fits said flange to removably retain said clip member in said cavity, said legs being on opposite sides of said cavity.

11. A disposable head ligating apparatus to ligate a body vessel comprising:

an applicator having as portions thereof first and second elongated members each having a handle portion, a jaw portion, and means to connect portions of said first and second elongated members so that the jaws may be closed together and then opened;

a ligating clip assembly comprising as separate members a first and second clip member, each clip member having a body portion and means to interlock said clip member with the other clip member upon clamping the clip members together;

a pair of disposable head means one of which is removably fitted on each of said jaw portion, each head means removably retaining one of said clip members prior to closing said jaws and expelling said clip member from said head upon closing said jaw portions, each of said head means including flexible remaining legs on opposite sides of each of said clip members, said legs being positioned opposite corresponding legs on the other head means, and a retaining cavity means to retain one of said clip members prior to closing of said jaw portions, which retaining cavity means is opened by the spreading apart of the legs which deforms and opens the cavity means releasing the clip member upon closing of said jaw portions and, said jaw portions applying pressure to said clip members to interlock said clip members together and then said jaw portions are opened leaving said clip members closed and interlocked on said vessel.

12. A ligating apparatus as in claim 11 wherein each of said head means retains one of said clip members by frictional fit, said legs being on opposite sides of said cavity means.

13. A ligating apparatus as in claim 12 wherein said cavity means is a curved sector in original shape and is flattened out upon closure of said jaws to expel said clip member.

14. A ligating apparatus as in claim 12 wherein each of said heads has four legs, with two legs arranged on each side of the cavity means.

15. A ligating apparatus as in claim 11 wherein each of said cavity means has a flange, each of said clip members has an indentation which fits said flange to removably retain said clip member in said cavity means, said legs being on opposite sides of said cavity means.

16. A ligating apparatus as in claim 11 wherein said clip assembly is of body-compatible plastic material.

17. A ligating apparatus as in claim 11 wherein said clip assembly is of a body-compatible plastic material which is absorbable in the body.

18. A ligating apparatus as in claim 11 wherein each of said clip members has a body portion and near one end thereof a male boss member and near the opposite end thereof a female identation to interlock with the corresponding boss on the opposite clip member.

19. A ligating apparatus as in claim 11 wherein said heads are of plastic and said clip assembly is of a different plastic.

20. A ligating apparatus to ligate a body vessel comprising:

an applicator having as portions thereof first and second elongated members each having a handle portion and a jaw portion, means to connect portions of said first and second elongated members so that the jaws may be closed together and then opened;

a ligating clip assembly comprising as separate members a first and second clip member, each clip member having a body portion and means on each body portion to interlock said clip member with the other clip member upon clamping the clip member together;

automatic clip feeding means to automatically feed clip members in sequence with one clip member being fed to each one of said jaw portions prior to closing said jaws, the jaw expelling said clip member from said jaw portion upon closing said jaw portions, each of said jaw portions having a retaining cavity means to removably retain one of said clip members, flexible retaining legs on opposite sides of each of said clip members, said legs being positioned opposite corresponding legs on the other jaw portion, the said legs, upon closing of the jaw portions, being spread apart and deforming said cavity means to open said cavity means and release said clip members from said jaw portions, said jaw portions then applying pressure to said clip members to clamp them together and then being opened leaving said clip members closed and clamped on said vessel.

21. A ligating apparatus as in claim 20 wherein, said legs are on opposite sides of said cavity.

22. A ligating apparatus as in claim 21 wherein said cavity is a curved sector in original shape and is flattened out upon closure of said jaws to expel said clip member.

23. A ligating apparatus as in claim 20 wherein each of said jaw portions has four legs, with two legs arranged on each side of the cavity.

24. A ligating apparatus as in claim 20 wherein said clip assembly is of body-compatible plastic material.

25. A ligating apparatus as in claim 20 wherein said clip assembly is of body-compatible plastic material which is absorable in the body.

26. A ligating apparatus as in claim 20 wherein each of said clip members has a body portion and near one end thereof a male boss member and near the opposite end thereof a female indentation to interlock with the corresponding boss on the opposite clip member.

27. A method to ligate a body tissue comprising:
    manually holding near said vessel an applicator having first and second elongated members each having a handle portion and a jaw portion and means to connect the portions of said first and second elongated members;
    ligating the body tissue using a ligating clip assembly comprising as separate members a first and a second clip member having a body portion and means to interlock said clip member with the other clip member upon clamping the clip members together;
    retaining one of said clip members in a cavity in each one of said jaw portions prior to closing said jaw portions and expelling said clip member from said cavity by deforming the cavity to open the cavity upon closing said jaw portions, said applicator including flexible retaining legs on opposite sides of each of the clip members;
    closing the jaw portions together to release the clip members from the cavities and interlock the clip members together and then spreading the jaw portions open;
    said applicator legs being positioned opposite corresponding legs on the other jaw portion, the said legs, upon closing of the jaws, being spread apart and deformationally opening the cavities to release said clip members from said jaw portions.

28. A ligating method as in claim 27 wherein, said legs are on opposite sides of said cavity.

29. A ligating method as in claim 27 wherein each of said cavity portions has a flange, each of said clip members has a channel which fits said flange to removably retain said clip member in said cavity, said legs being on opposite sides of said cavity.

30. A ligating method as in claim 27 wherein said cavity is originally a spherical sector and is flattened out to an elliptical sector.

31. A ligating method as in claim 27 wherein each of said jaw portions has four legs, with two legs arranged on each side of the cavity.

32. A ligating method as in claim 27 wherein each of said clip members has a rod body portion and near one end thereof a male boss member and near the opposite end thereof a female indentation to interlock with the corresponding boss on the opposite clip member.

* * * * *